(12) United States Patent
Schaefer

(10) Patent No.: US 8,877,735 B2
(45) Date of Patent: Nov. 4, 2014

(54) ALKOXYLATED SUCROSE ESTERS COMPOSITION

(75) Inventor: Jared John Schaefer, Wyoming, OH (US)

(73) Assignee: The Procter & Gamble Company, Cincinnati, OH (US)

(*) Notice: Subject to any disclaimer, the term of this patent is extended or adjusted under 35 U.S.C. 154(b) by 815 days.

(21) Appl. No.: 11/157,010

(22) Filed: Jun. 20, 2005

(65) Prior Publication Data

US 2006/0047109 A1 Mar. 2, 2006

Related U.S. Application Data

(60) Provisional application No. 60/606,075, filed on Aug. 31, 2004.

(51) Int. Cl.

| | | |
|---|---|---|
| A61K 31/7016 | (2006.01) | |
| A61K 31/70 | (2006.01) | |
| A61K 31/715 | (2006.01) | |
| C11D 1/825 | (2006.01) | |
| C07H 15/08 | (2006.01) | |
| C10M 145/38 | (2006.01) | |
| C11D 3/20 | (2006.01) | |
| C07H 15/06 | (2006.01) | |
| C07H 13/06 | (2006.01) | |
| C08G 65/26 | (2006.01) | |
| A23L 1/308 | (2006.01) | |
| C11D 3/30 | (2006.01) | |
| B01F 17/00 | (2006.01) | |
| C11D 1/74 | (2006.01) | |
| C10M 129/76 | (2006.01) | |
| C10M 129/74 | (2006.01) | |
| C11D 1/66 | (2006.01) | |
| C11D 1/83 | (2006.01) | |
| C10M 173/00 | (2006.01) | |
| C11D 1/29 | (2006.01) | |
| C11D 1/75 | (2006.01) | |
| C11D 1/14 | (2006.01) | |
| C11D 1/72 | (2006.01) | |

(52) U.S. Cl.
CPC ........... *B01F 17/0085* (2013.01); *C11D 1/825* (2013.01); *C11D 1/29* (2013.01); *C07H 15/08* (2013.01); *C10M 145/38* (2013.01); *C10N 2230/24* (2013.01); *C11D 3/2013* (2013.01); *C10M 2207/283* (2013.01); *C11D 1/75* (2013.01); *C07H 15/06* (2013.01); *C07H 13/06* (2013.01); *C08G 2650/26* (2013.01); *C10M 2203/102* (2013.01); *C08G 65/2615* (2013.01); *A23L 1/3088* (2013.01); *C10N 2230/04* (2013.01); *C11D 3/30* (2013.01); *C08G 65/2648* (2013.01); *C10M 2207/289* (2013.01); *B01F 17/0028* (2013.01); *C11D 1/146* (2013.01); *C11D 1/74* (2013.01); *C10M 129/76* (2013.01); *C10M 129/74* (2013.01); *C11D 1/667* (2013.01); *C11D 1/83* (2013.01); *C10M 173/00* (2013.01); *C11D 1/72* (2013.01); *C10M 2203/1025* (2013.01); *B01F 17/0092* (2013.01); *C10M 2209/104* (2013.01); *B01F 17/0021* (2013.01)
USPC ........................... 514/53; 514/23; 536/123.13

(58) Field of Classification Search
USPC ................................ 514/53, 23; 536/123.13
See application file for complete search history.

(56) References Cited

U.S. PATENT DOCUMENTS

| | | | |
|---|---|---|---|
| 3,102,114 A | 8/1963 | Komori et al. | |
| 3,277,080 A | 10/1966 | Nobile | |
| 3,435,024 A | 3/1969 | Nobile et al. | |
| 3,714,144 A | 1/1973 | Feuge et al. | |
| 3,963,699 A | 6/1976 | Rizzi et al. | |
| 3,996,206 A * | 12/1976 | Parker et al. | 536/119 |
| 4,380,616 A | 4/1983 | Vance et al. | |
| 4,915,965 A * | 4/1990 | Tanaka | 426/282 |
| 5,077,073 A * | 12/1991 | Ennis et al. | 426/531 |
| 5,118,448 A | 6/1992 | Cooper | |
| 5,362,894 A | 11/1994 | Handwerker et al. | |
| 5,427,815 A | 6/1995 | Ferenz | |
| 5,512,313 A | 4/1996 | Cooper et al. | |
| 6,486,120 B1 * | 11/2002 | Porta et al. | 510/515 |

FOREIGN PATENT DOCUMENTS

| | | | |
|---|---|---|---|
| CN | 1180475 | * | 5/1998 |
| EP | 0415635 A1 | * | 3/1991 |

OTHER PUBLICATIONS

Jandacek et al. (Chemistry and Physics of Lipids (1978), 22 (2), 163-176) (Abstract Sent).*
Abstract of Liu et al.; CN 1180475; May 6, 1998 (abstract sent).*
Feuge, et al.; "Journal of American Oil Chem. Soc.", 1970, 47 (2) pp. 56-60.

* cited by examiner

*Primary Examiner* — Shaojia Anna Jiang
*Assistant Examiner* — Michael C Henry
(74) *Attorney, Agent, or Firm* — Melissa G Krasovec; Melody Jones

(57) ABSTRACT

Purified alkoxylated sucrose esters of the formula:

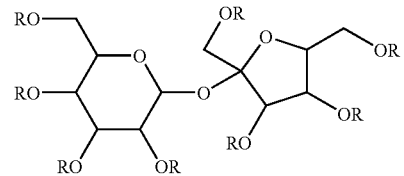

wherein R is independently selected from: COR'; $(CH_2CH_2O)_xH$; and $(CH_2CH_2O)_x$ COR'; wherein R' is a fatty acid compound having from about 2 to about 28 carbon atoms; and wherein x is a number selected from about 1 to about 50; wherein at least one of the R groups is an ester group that is directly esterified to the sucrose backbone; and wherein the alkoxylated sucrose ester composition further comprises: less than 1% aldehydes; less than 1% ketones; less than 1% benzyl halide; less that 1% mono-benzyl ether; less than 1% acetals; and less than 1% ketals.

20 Claims, No Drawings

ALKOXYLATED SUCROSE ESTERS COMPOSITION

CROSS REFERENCE TO RELATED APPLICATIONS

This application claims the benefit of priority to U.S. Provisional Application Ser. No. 60/606,075, filed Aug. 31, 2004, which is herein incorporated by reference.

BRIEF DESCRIPTION OF THE INVENTION

The present invention relates to alkoxylated sucrose esters having a degree of alkoxylation per available hydroxyl of about 1 to about 50 and a degree of esterification of about 1 to 7.5 having increased purity. More particularly, this invention relates to alkoxylated sucrose esters of novel structure made from the improved process disclosed herein.

BACKGROUND OF THE INVENTION

Alkoxylated sucrose esters are useful as surfactants, lubricants, emulsifiers, and cleaning agents. By varying the degree of esterification, the properties of the alkoxylated sucrose esters can range from those useful for emulsifiers, aqueous-based surfactants, etc. (generally lower esterification) to those useful for oil-soluble surfactants, cleaning agents, etc. (generally higher esterification).

Several methods are known for producing sucrose esters with varying degrees of esterification. For instance, Rizzi and Taylor, U.S. Pat. No. 3,963,699, describe a solvent-free transesterification process in which a mixture of a polyol (such as sucrose), a fatty acid lower alkyl ester (such as a fatty acid methyl ester), an alkali metal fatty acid soap, and a basic catalyst is heated to form a homogenous melt, to which is added excess fatty acid lower alkyl ester to form the higher polyol fatty acid polyesters.

Feuge et al, U.S. Pat. No. 3,714,144, and Feuge et al, *J. Amer. Oil Chem. Soc.*, 1970, 47(2), 56-60, disclose a solvent-free transesterification process which includes mixing molten sucrose with esters of fatty acids and alkali-free sodium or potassium soaps under a partial vacuum. The teachings of Feuge et al are generally directed to the formation of lower esters; the only specific teaching by Feuge et al of a method in which the percentage of sucrose esters having three or more fatty acid chains is greater than 35% of the total sucrose esters formed uses methyl carbitol palmitate as a fatty acid source.

Osipow et al, U.S. Pat. No. 4,380,616, disclose the preparation of sucrose mono- and di-esters by forming a transparent emulsion containing immiscible reactants and maintaining the transparent emulsions under appropriate conditions to permit reaction. Sucrose mono- and di-esters are formed using emulsions containing methyl fatty acid ester and sucrose. Osipow et al also disclose the formation of mono- and di-glycerides using emulsions containing glycerine and methyl fatty acid esters or glycerol tri-esters.

Also known are various methods for producing alkoxylated sucrose esters. Ennis et al, U.S. Pat. No. 5,077,073, disclose a process for preparing alkoxylated sucrose esters made from alkoxylated sucrose that is reacted in a solvent to form the alkoxylated sucrose esters. This material then may be used as a fat substitute. Ferenz, U.S. Pat. No. 5,427,815, discloses the process for preparing linked, alkoxylated, esterified polyols made from alkoxylated polyols that are then esterified with a polycarboxylate segment. Handwerker et al, U.S. Pat. No. 5,362,894 and Cooper et al, U.S. Pat. No. 5,512,313, disclose similar processes for preparing alkoxylated esterified polyols made from alkoxylated polyols that are then esterified. Porta et al, U.S. Pat. No. 6,486,120, disclose the use of alkoxylated sucrose esters in liquid, aqueous softening compositions. Again, the methodology disclosed involves first alkoxylating the sucrose in a solvent and then esterifying to form the alkoxylated sucrose esters.

Cooper, U.S. Pat. No. 5,118,448, discloses a process for preparing alkoxylated esterified polyols that involves first reacting a benzylated polyol with an epoxide. The process to form the benzylated polyol raw material involves a reaction between a polyol and an aldehyde or ketone to form an acetal or ketal. The acetal or ketal is then reacted with alkali metal and benzyl halide to give the mono-benzyl ether of the acetal or ketal. This mono-benzyl ether is then hydrolyzed in the presence of dilute acid to give the benzylated polyol. The benzylated polyol is then reacted with epoxide to form an alkoxylated, benzylated polyol. The resulting mixture is then reacted with hydrogen to convert the benzyl group to a hydroxyl group. The hydroxyl group is then esterified using a fatty acid compound such as a fatty acid, fatty acid ester, or fatty acid halide. Like the processes previously described, this process involves alkoxylating prior to esterifying, though it claims to produce a material with at least one ester group directly bonded to the polyol backbone.

Generally, these known processes for making alkoxylated sucrose esters suffer from the requirement of using a solvent to first alkoxylate the sucrose. In the case of Cooper, U.S. Pat. No. 5,118,448, a solvent would be required to first benzylate the sucrose, as this step precedes the alkoxylation step. The use of a solvent to dissolve sucrose results in solvent present as an impurity in the final product and/or undesirable side reactions between the solvent and other elements which produce unwanted reaction products.

For instance, Cooper, U.S. Pat. No. 5,118,448, discloses a process for producing a material with at least one ester group bonded directly to the polyol backbone. However, this process will also undoubtedly produce unwanted by-products. These by-products may be produced in one or more of several ways. First, they may be formed during the formation of the benzylated polyol from the starting polyol, which typically involves reacting the polyol with either an aldehyde or a ketone to form an acetal or a ketal. These acetals or ketals are then reacted with alkali metal and benzyl halide to produce the mono-benzyl ether of the acetal or ketal. The mono-benzyl ether is then reacted with dilute acid and water to form the benzylated polyol. Secondly, by-products may be formed when the benzylated, alkoxylated polyol is then reacted with hydrogen in the presence of a transition metal hydrogenalysis catalyst to form the alkoxylated polyol. These by-products may include unremoved aldehydes, ketones, acetals, ketals, mono-benzyl ethers, and benzyl halide.

By-products such as these are problematic because they affect the functionality of the individual alkoxylated sucrose ester and may have a negative impact on the purity of a finished product that incorporates such alkoxylated sucrose esters. Furthermore, should these alkoxylated sucrose esters be approved for use in food products, such by-products will in all likelihood be banned from inclusion in such food products.

Accordingly, there is a need for alkoxylated sucrose esters having reduced levels of by-products and processes for producing such improved alkoxylated sucrose esters.

SUMMARY OF THE INVENTION

The present invention relates to alkoxylated sucrose ester compositions with increased purity, wherein the alkoxylated sucrose ester composition comprises:

a) at least one alkoxylated sucrose ester having the following structure:

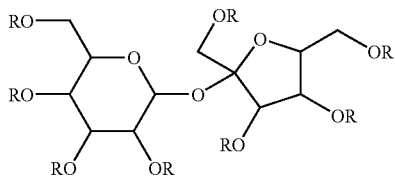

wherein R is independently selected from:
  i) COR';
  ii) $(CH_2CH_2O)_xH$; and
  iii) $(CH_2CH_2O)_x COR'$;
wherein R' is a fatty acid compound having from about 2 to about 28 carbon atoms; and wherein x is a number selected from about 1 to about 50; wherein at least one of the R groups is an ester group that is directly esterified to the sucrose backbone; and
  b) wherein the alkoxylated sucrose ester composition further comprises:
    i) less than 1% aldehydes;
    ii) less than 1% ketones;
    iii) less than 1% benzyl halide;
    iv) less than 1% mono-benzyl ether;
    v) less than 1% acetals; and
    vi) less than 1% ketals.

In one embodiment the present invention relates to a lubricating composition comprising such an alkoxylated sucrose ester composition or mixtures thereof according to above and an additional lubricant selected from olefins, paraffins, and mixtures thereof. In one embodiment, the lubricating composition further comprises water.

In one embodiment, the present invention relates to a surfactant composition comprising an alkoxylated sucrose ester composition according to above and an additional surfactant selected from amine oxides, fatty alcohols, alkoxylated alcohols, sulfated alcohols, alkoxylated sulfated alcohols, and mixtures thereof.

In one embodiment, the present invention relates to an emulsifier composition comprising an alkoxylated sucrose ester composition according to above and an emulsifier selected from glycerine esters, sorbitan esters, and mixtures thereof.

In one embodiment, the present invention relates to a food composition comprising an alkoxylated sucrose ester composition according to above and an additional sucrose ester.

In one embodiment, the present invention relates to a laundry composition comprising an alkoxylated sucrose ester composition according to above and further comprising an additional material selected from amines, cationic amines, water, and mixtures thereof.

In one embodiment, the present invention relates to a purified alkoxylated sucrose ester composition, wherein the composition comprises:

a) an alkoxylated sucrose ester having the following structure:

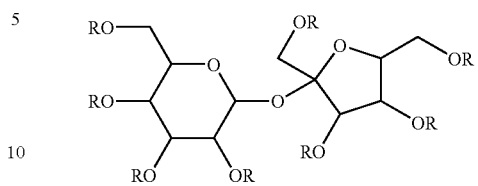

wherein R is independently selected from:
  i) COR';
  ii) $(CH_2CH_2O)_xH$; and
  iii) $((CH_2CH_2O)_x COR'$;
wherein R' is a fatty acid compound having from about 2 to about 28 carbon atoms and x is from about 1 to about 50; and
wherein at least one of the R groups is an ester directly esterified to the sucrose backbone; and
  b) wherein the alkoxylated sucrose ester composition further comprises:
    i) less than about 100 ppm aldehydes;
    ii) less than about 100 ppm ketones;
    iii) less than about 100 ppm benzyl halide;
    iv) less than about 100 ppm mono-benzyl ether;
    v) less than about 100 ppm acetals; and
    vi) less than about 100 ppm ketals.

In one embodiment, the present invention relates to a lubricating composition comprising such an alkoxylated sucrose ester composition or mixtures thereof and an additional lubricant selected from olefins, paraffins, and mixtures thereof.

In one embodiment, the present invention relates to a lubricating composition according above wherein the composition further comprises water.

In one embodiment, the present invention relates to a surfactant composition comprising an alkoxylated sucrose ester composition according to claim 8 and an additional surfactant selected from amine oxides, fatty alcohols, alkoxylated alcohols, sulfated alcohols, alkoxylated sulfated alcohols, and mixtures thereof.

In one embodiment, the present invention relates to an emulsifier composition comprising an alkoxylated sucrose ester composition according to above and an emulsifier selected from glycerine esters, sorbitan esters, and mixtures thereof.

In one embodiment, the present invention relates to a food composition comprising an alkoxylated sucrose ester composition according to above and an additional sucrose ester.

In one embodiment, the present invention relates to a laundry composition comprising an alkoxylated sucrose ester composition according to above and further comprising an additional material selected from amines, cationic amines, water, and mixtures thereof.

In one embodiment, the present invention relates to a purified alkoxylated sucrose ester composition, wherein the composition comprises:

a) an alkoxylated sucrose ester having the following structure:

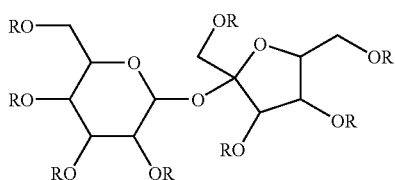

wherein R is independently selected from:
  ii) COR';
  iii) $(CH_2CH_2O)_xH$; and
  iv) $((CH_2CH_2O)_x COR')$;
wherein R' is a fatty acid compound having from about 2 to about 28 carbon atoms and x is from about 1 to about 50; and
wherein at least one of the R groups is an ester directly esterified to the sucrose backbone; and
b) wherein the alkoxylated sucrose ester composition is:
  i) free of aldehydes;
  ii) free of ketones;
  iii) free of benzyl halide;
  iv) free of mono-benzyl ether;
  v) free of acetals; and
  vi) free of ketals.

In one embodiment, the present invention relates to a lubricating composition comprising an alkoxylated sucrose ester composition or mixtures thereof according to above and an additional lubricant selected from olefins, paraffins, and mixtures thereof.

In one embodiment, the present invention relates to a surfactant composition comprising an alkoxylated sucrose ester composition according to above and an additional surfactant selected from amine oxides, fatty alcohols, alkoxylated alcohols, sulfated alcohols, alkoxylated sulfated alcohols, and mixtures thereof.

In one embodiment, the present invention relates to an emulsifier composition comprising an alkoxylated sucrose ester composition according to above and an emulsifier selected from glycerine esters, sorbitan esters, and mixtures thereof.

In one embodiment, the present invention relates to a food composition comprising an alkoxylated sucrose ester composition according to above and an additional sucrose ester.

In one embodiment, the present invention relates to a laundry composition comprising an alkoxylated sucrose ester composition according to above and further comprising an additional material selected from amines, cationic amines, water, and mixtures thereof.

DETAILED DESCRIPTION OF THE INVENTION

A. Definitions

Various publications and patents are referenced throughout this disclosure. All references cited herein are hereby incorporated by reference. Unless otherwise indicated, all percentages and ratios are calculated by weight and at atmospheric pressure and standard temperature. All percentages and ratios are calculated based on the total dry composition unless otherwise indicated.

All component or composition levels are in reference to the active level of that component or composition, and are exclusive of impurities, for example, residual solvents or by-products, which may be present in commercially available sources.

Referred to herein are trade names for components including various ingredients utilized in the present invention. The inventors herein do not intend to be limited by materials under a certain trade name. Equivalent materials (e.g., those obtained from a different source under a different name or catalog number) to those referenced by trade name may be substituted and utilized in the compositions, kits, and methods herein.

As used herein, and unless otherwise indicated, the use of a numeric range to indicate the value of a given variable is not intended to be limited to just discrete points within that stated range. One of ordinary skill in the art will appreciate that the use of a numeric range to indicate the value of a variable is meant to include not just the values bounding the stated range, but also all values and sub-ranges contained therein. By way of example, consider variable X that is disclosed as having a value in the range of A to B. One of ordinary skill in the art will understand that variable X is meant to include all integer and non-integer values bounded by the stated range of A to B. Moreover, one of ordinary skill in the art will appreciate that the value of the variable also includes all combinations and/or permutations of sub-ranges bounded by the integer and non-integer values within and including A and B.

In the description of the invention various embodiments and/or individual features are disclosed. As will be apparent to the ordinarily skilled practitioner, all combinations of such embodiments and features are possible and can result in preferred executions of the present invention.

B. Improved Process for Preparing Alkoxylated Sucrose Esters and the Products Thereof The improved process and products of the present invention involve alkoxylating sucrose esters or mixtures thereof that have already been esterified to a varying degree using any of the commonly known processes for sucrose esterification. These alkoxylated sucrose esters may exhibit interesting properties as surfactants, lubricants, emulsifiers, and cleaning agents, and should exhibit different properties from both the starting sucrose esters or alkoxylated sucrose esters that are formed by prior processes of first alkoxylating the sucrose and then esterifying the alkoxylated sucrose. Without being limited by theory, it is believed that the improved alkoxylated sucrose esters are also advantageous as the process for preparing them is capable of being carried out without a solvent, avoiding the need for expensive additional purification processes. The previously known processes generally require the use of a solvent which must then be removed by a purification process.

Furthermore, without being limited by theory, it is believed that the novel processes disclosed herein also produce alkoxylated sucrose esters that are different in composition from those alkoxylated sucrose esters formed when sucrose is first esterified and then alkoxylated. Without being limited by theory, it is believed that this is due to the fact that when sucrose is first alkoxylated and then esterified, as in the previous processes, all of the ester groups reside some distance away from the sucrose molecule based on the number of alkoxyl groups reacted with the hydroxyls of the sucrose, as the hydroxyl sites for esterification are moved away from the molecule by the alkoxyl groups. In contrast, when utilizing the processes of the present invention for preparing alkoxylated sucrose esters, when the sucrose is first esterified and then alkoxylated, the ester groups now exist on the sucrose molecule itself, and generally do not move to locations farther away from the sucrose as the alkoxylation progresses. For this reason, the composition and performance of the alkoxylated sucrose esters made using the improved process set forth herein are different from those exhibited by the alkoxylated sucrose esters prepared using previously disclosed processes.

The present invention therefore encompasses alkoxylation processes for the production of alkoxylated sucrose esters. The present invention will now be described in detail with reference to specific embodiments. In general, the process for the preparation of alkoxylated sucrose esters of the present invention comprises the steps of forming an initial reaction product from an initial reaction mixture; and optionally purifying the reaction product and removing any isolated impurities and/or unreacted components.

Alkoxylated Sucrose Esters

As used herein, "sucrose esters" are defined as sucrose molecules that have been esterified with between, on average, one to eight ester groups on the eight available hydroxyls. Depending on their degree of esterification, sucrose esters can either be solids or liquids.

These sucrose esters or mixtures thereof can then be alkoxylated according to the processes of the present invention by reacting them with an epoxide or mixtures thereof, which involves a reaction at the non-esterified hydroxyl sites. Although this reaction can utilize a solvent if the starting sucrose ester is a solid or a liquid, no solvent is required. Because the addition of a solvent will likely require later removal of residual solvent through purification techniques, it is preferable that a solvent is not used during the alkoxylation.

A comparison of the chemical structures of the alkoxylated sucrose esters according to the present invention and those which result from previously known processes can be illustrated by referring to FIG. 1. For illustration purposes, the molecule in FIG. 1 is assumed to have been reacted with ethylene oxide, a common epoxide. This is not intended to limit the scope of the disclosed compositions to this one type of alkoxylated sucrose ester. The general structure shown in FIG. 1 is intended to generally represent both the composition that results when the previously known processes or the processes of the present invention are utilized. The differences between the resulting compositions are highlighted by the discussion below.

General Structure of Alkoxylated Sucrose Ester

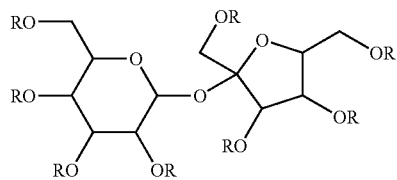

FIG. 1 wherein R is independently selected from
i) COR' (ester group)
ii) $(CH_2CH_2O)_xH$ (ethoxide group, where x=1-50)
iii) $((CH_2CH_2O)_x COR'$ (ethoxide group that has been esterified, where x=1-50)
where R' is independently selected from alkyl groups The number of ester groups, ethoxide groups, and esterified ethoxide groups on the sucrose depends on the order in which the esterification and ethoxylation are carried out. In the case of the known processes where sucrose is first ethoxylated and then esterified, the resulting molecules have ester groups existing as esters on the end of a number of ethoxide groups (structure iii). These materials will not have any ester groups directly esterified to the sucrose backbone (structure i), as the sites for esterification were already moved away from the sucrose backbone during the previous ethoxylation step. In contrast, in the compositions of the present invention, there will be a finite number of ester groups that are directly bonded to the sucrose backbone, as the starting raw material is a sucrose ester, which by definition consists of ester groups directly esterified to the hydroxyls of sucrose. These sucrose esters are then ethoxylated, which produces ethoxide groups as shown by structure ii. There will be a certain amount of ester groups that move from being directly bonded to the sucrose polyol (structure i) to the ends of the ethoxide groups (structure iii), however, at least some of the ester groups do remain directly bonded to the sucrose.

The alkoxylated sucrose ester compositions herein have increased purity and the alkoxylated sucrose ester composition contains at least one alkoxylated sucrose ester having the following structure:

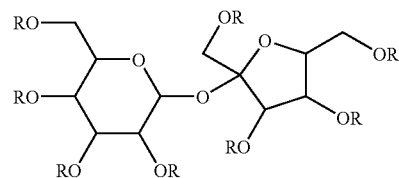

wherein R is independently selected from:
i) COR';
ii) $(CH_2CH_2O)_xH$; and
iii) $(CH_2CH_2O)_x COR'$;
wherein R' is a fatty acid compound having from about 2 to about 28 carbon atoms; and wherein x is a number selected from about 1 to about 50;
wherein at least one of the R groups is an ester group that is directly esterified to the sucrose backbone; and
the alkoxylated sucrose ester composition further comprises:
i) less than 1% aldehydes;
ii) less than 1% ketones;
iii) less than 1% benzyl halide;
iv) less than 1% mono-benzyl ether;
v) less than 1% acetals; and
vi) less than 1% ketals.

In one embodiment, the alkoxylated sucrose ester composition comprises
i) less than about 100 ppm aldehydes;
ii) less than about 100 ppm ketones;
iii) less than about 100 ppm benzyl halide;
iv) less than about 100 ppm mono-benzyl ether;
v) less than about 100 ppm acetals; and
vi) less than about 100 ppm ketals.

In one embodiment, the alkoxylated sucrose ester composition is free of aldehydes; free of ketones; free of benzyl halide; free of mono-benzyl ether; free of acetals; and free of ketals.

Suitable Alkoxylated Sucrose Esters of the present invention may be prepared by the following process:

Sucrose esters are defined as sucrose molecules that have been esterified with between, on average, one to eight ester groups on the eight available hydroxyls. Depending on their degree of esterification, sucrose esters can either be solids or liquids. These sucrose esters or mixtures thereof can then be alkoxylated by reacting them with epoxide or mixtures thereof, which involves a reaction at the non-esterified hydroxyl sites. This reaction may utilize a solvent if the starting sucrose ester is a solid or a liquid, or alternately, does not require a solvent when the starting sucrose esters or mixtures thereof are a liquid.

The improved processes of the present invention involve alkoxylating sucrose esters or mixtures thereof that have already been esterified to a varying degree using any of the commonly known processes for sucrose esterification. Without being limited by theory, it is believed that these alkoxylated sucrose esters exhibit interesting properties as surfactants, lubricants, and cleaning agents, and exhibit different properties from either the starting sucrose esters or those alkoxylated sucrose esters formed by the previously known processes of first alkoxylating sucrose and then esterifying.

It has now been surprisingly found that the improved processes of the present invention produce alkoxylated sucrose esters that are different in composition from those alkoxylated sucrose esters formed when sucrose is first alkoxylated and then esterified. Without being limited by theory, when the sucrose is first esterified and then alkoxylated, it is believed that at least some of the ester groups now exist on the sucrose molecule itself, and may or may not move to locations farther away from the sucrose as the alkoxylation progresses. It is believed that, for this reason, the composition and performance of the alkoxylated sucrose esters made using the improved processes herein are different from that exhibited by the alkoxylated sucrose esters prepared using processes previously known.

The chemical structures of the composition resulting from the processes disclosed herein and that which results from the prior art can be illustrated by FIG. 1. For illustration purposes, the molecule in FIG. 1 is assumed to have been reacted with ethylene oxide, a common epoxide. This is not intended to limit the scope of the disclosed composition to this one type of alkoxylated sucrose ester. The general structure shown in FIG. 1 is intended to represent both the composition that results when the prior art or the disclosed process is utilized, and the differences described in the previous paragraph are highlighted by the discussion below.

General Structure of Alkoxylated Sucrose Ester

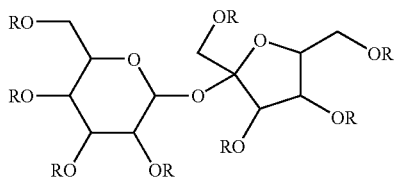

FIG. 1 where R is independently selected from:
  iv) COR' (ester group);
  v) $(CH_2CH_2O)_xH$ (ethoxide group, where x=1-50);
  vi) $((CH_2CH_2O)_x COR'$ (ethoxide group that has been esterified, where x=1-50); and
  vii) mixtures thereof.

Without being limited by theory, it is now believed that the number of ester groups, ethoxide groups, and esterified ethoxide groups on the sucrose depends on the order in which the esterification and ethoxylation are carried out. In the case of the previously known processes where the sucrose was first ethoxylated and then esterified, the resulting molecules have ester groups existing as esters on the end of a number of ethoxide groups (i.e., structure iii). These materials will not have any ester groups directly esterified to the sucrose backbone (structure i), as the sites for esterification have been moved away from the sucrose backbone during the previous ethoxylation step. In contrast, the alkoxylated sucrose esters resulting from the novel processes disclosed herein, will have a finite number of ester groups that exist directly bonded to the sucrose backbone, as the starting raw material is a sucrose ester, which by definition consists of ester groups directly esterified to the hydroxyls of sucrose. By the processes herein, these sucrose esters are then ethoxylated, which produces ethoxide groups as shown by structure ii.

Therefore, the present invention encompasses alkoxylation processes for the production of alkoxylated sucrose esters. The present invention will now be described in detail with reference to specific embodiments.

In general, the processes for the preparation of alkoxylate sucrose esters of the present invention include the steps of forming an initial reaction product from an initial reaction mixture; optionally washing the reaction product to remove impurities; optionally sparging the reaction product with nitrogen; optionally subjecting the reaction product to a vacuum; and optionally drying a purified reaction product. Preferably, no reaction solvent is used during the preparation process so that there is no reaction solvent residual to be removed.

Initial Reaction Mixture

An initial reaction mixture is formed by adding sucrose esters, or mixtures thereof, to a suitable reaction vessel. The initial reaction mixture contains a sucrose ester and a catalyst. In one embodiment, the initial reaction mixture contains a solvent.

In one embodiment, the initial reaction mixture contains from about 0.1% to about 99.99%, by weight of the initial reaction mixture, of the sucrose ester. Preferably, the initial reaction contains from about 90% to about 99.9%, by weight of the initial reaction mixture, of the sucrose ester, alternatively from about 95% to about 99%, still alternatively from about 97% to about 99%. Suitable sucrose esters for use herein include those having an average degree of esterification of from about 1% to about 99%, preferably having a degree of esterification of from about 25% to about 90%, alternatively from about 30% to about 80%. Sucrose esters useful herein include sucrose mono, di, tri, tetra, penta, hexa, and heptaesters.

In one embodiment, the initial reaction mixture comprises from about 0.01% to about 99%, by weight of the initial reaction mixture, of an alkoxylation catalyst. Preferably, the initial reaction mixture comprises from about 1% to about 10%, by weight of the initial reaction mixture, of the catalyst, alternatively from about 2% to about 5%. Suitable catalysts for use herein include sodium metals, potassium metals, sodium/potassium alloys, and mixtures thereof.

In one embodiment, the initial reaction mixture contains a solvent. Optionally, a solvent may be used (although not preferred) if the sucrose esters or mixtures thereof do not form a liquid reaction medium. When present, the initial reaction mixture may comprise from about 0.01% to about 99.89% of a solvent. Preferably, the initial reaction mixture comprises less than 5% of solvent, alternatively less than about 1% of solvent, alternatively is substantially free of solvent. As used herein, "substantially free of solvent" refers to a composition which comprises no readily detectable level of solvent. When included, solvents that may be used herein include materials such as dimethyl sulfoxide and/or dimethyl formamide.

The reaction vessel may be set up such that the epoxide or mixtures thereof can also be added at the time the initial reaction product is to be made.

Initial Reaction Product

The alkoxylated sucrose esters of the present invention are formed by first forming an initial reaction product. The initial reaction product is formed by reacting the initial reaction mixture with an epoxide. The initial reaction mixture and the epoxide are preferably reacted for a period of time in the range of from about 30 minutes to about 6 hours and at a temperature in the range of from about 80° C. to about 120° C.

The ratio of the epoxide to the sucrose ester is selected such that the mole ratio of epoxide groups to sucrose hydroxyls is from about 1 to about 100, alternatively from about 1 to about 50; alternatively from about 1 to about 30; alternatively from about 1 to about 20.

Typically, initial reaction product is formed by reacting the initial reaction mixture in a vessel containing an atmosphere that includes the epoxide and may include an inert gas, such as nitrogen. Epoxides suitable for use herein include ethylene oxide, propylene oxide, butylene oxide, and mixtures thereof. In one embodiment, the initial reaction product is formed while the epoxide is injected into the atmosphere around the initial reaction mixture. In another embodiment, the initial reaction product is formed in a reactor wherein the epoxide is injected into the atmosphere of the reactor. In one embodiment, the epoxide is added to the atmosphere of the initial reaction mixture in a continuous feed until the requisite amount of epoxide has been added.

In one embodiment, the initial reaction mixture is reacted in the atmosphere for a period of time in the range of from about 10 minutes to about 12 hours, and at a temperature in the range of from about 80° C. to about 120° C. The atmosphere within the reactor can be in the range from about 0.1% to 100% of the epoxide, or alternately, may also contain from about 0% to 99.9% of an inert gas such as nitrogen. The epoxide or mixtures thereof is reacted with the sucrose esters or mixtures thereof until the desired amount of alkoxyl groups has been added to the hydroxyl sites of the sucrose ester.

Purification

Optionally, the alkoxylated sucrose esters may be purified by adding between about 1% to about 50% by weight of the initial reaction product, of water and/or alcohol at a temperature between about 20° C. and 100° C., gently stirring, and allowing the two phases to separate. The aqueous or alcohol phase can then be removed by traditional separation means, the impurities isolated from the purified reaction product and the purified alkoxylated sucrose ester phase is retained. Suitable alcohols for the purification include methanol, ethanol, propanol, and butanol. Alternately, if this water or alcohol washing step does not remove the desired impurities or if it is undesirable to add water or alcohol, the alkoxylated sucrose esters may be sparged with an inert gas such as nitrogen and/or subjected to a vacuum to remove any unreacted epoxide.

Uses for Alkoxylated Sucrose Esters Having Increased Purity

The alkoxylated sucrose esters described herein may have a variety of uses. Such alkoxylated sucrose esters may be included in various products compositions such as lubricating compositions, surfactants, emulsifiers, foods, and laundry products (detergents, softeners, fabric treatments and the like). As such, the alkoxylated sucrose esters may be used either in their pure form, as mixtures with other alkoxylated sucrose esters having either different degrees of alkoxylation or esterification or both, as mixtures with other lubricants or additives, and/or as mixtures with other alkoxylated sucrose esters and other lubricants and additives. Due to the increased purity of the disclosed alkoxylated sucrose esters, the applicability of the materials is more varied. Without being limited by theory, it is believed that this is due to the fact that the alkoxylated sucrose esters enable less complex formulations due to the lower level of impurities as well as the fact that many of these applications require or prefer to avoid the impurities. These advantages are particularly seen in certain laundry applications where even minor impurities, can cause significant issues in formulation.

When the alkoxylated sucrose esters described herein are included in a lubricating composition, the composition may further contain additional materials commonly associated with known lubricating compositions. For instance, the composition may contain an additional lubricant selected from olefins, paraffins, and mixtures thereof. The lubricating composition may also contain water.

When the alkoxylated sucrose esters described herein are included in a surfactant composition, the surfactant composition may further contain additional materials commonly associated with known surfactant compositions. For instance, the composition may contain an additional surfactant selected from amine oxides, fatty alcohols, alkoxylated alcohols, sulfated alcohols, alkoxylated sulfated alcohols, and mixtures thereof.

When the alkoxylated sucrose esters described herein are included in an emulsifier composition, the emulsifier composition may further contain additional materials commonly associated with known emulsifier compositions. For instance, the emulsifier composition may further contain an emulsifier selected from glycerine esters, sorbitan esters, and mixtures thereof.

When the alkoxylated sucrose esters described herein are included in a food composition, the composition may further contain additional materials commonly associated with known food compositions. For instance, the composition may contain may further contain an additional sucrose ester.

When the alkoxylated sucrose esters described herein are included in a laundry composition they may further contain additional materials commonly associated with known laundry compositions. For instance, the composition may contain an additional material selected from amines, cationic amines, water, and mixtures thereof. Similarly, the composition may contain an additional material selected from surfactants, builders, enzymes, and deposition aids.

EXAMPLES

The following are non-limiting examples of alkoxylated sucrose esters, production and methods of making the same, in accordance with the present invention. The following examples are provided to illustrate the invention and are not intended to limit the spirit or scope thereof in any manner.

Example 1

Approximately 100 g of sucrose esters with an average degree of esterification of about 5 are prepared according to Rizzi and Taylor, U.S. Pat. No. 3,963,699. The sucrose esters are then placed in a reactor, and 1 g of sodium/potassium alloy is added to the reactor. The mixture is heated to 100° C. and 32 g of ethylene oxide is gradually fed into the reactor to maintain the system pressure to about 50 psi. The reaction is allowed to proceed for about 2 hours, or until all 32 g of the ethylene oxide is reacted with the sucrose esters and then the ethylene oxide feed is stopped. The initial reaction product is then cooled to 60° C. The initial reaction product now weighs approximately 132 g, which corresponds to an addition of, on average, 4 ethylene oxide groups on each of the three available hydroxyl groups.

The initial reaction product is then washed with 24 g of water at 60° C. The water and initial reaction product are gently stirred for approximately 10 minutes, and the resulting mixture is centrifuged. The top phase is decanted and retained and the bottom, aqueous phase is discarded.

The purified alkoxylated sucrose ester is analyzed and contains greater than 99.9% alkoxylated sucrose ester; less than 0.01% aldehyde; less than 0.01% ketones; less than 0.01% benzyl halide; less than 0.01% mono-benzyl ether; less than 0.01% acetals; and less than 0.01% ketals.

Example 2

Approximately 100 g of sucrose esters with an average degree of esterification of about 4 are prepared according to Rizzi and Taylor, U.S. Pat. No. 3,963,699. The sucrose esters are then placed in a reactor, and 1 g of sodium/potassium alloy is added to the reactor. The mixture is heated to 100° C. and 125 g of ethylene oxide is gradually fed into the reactor to maintain the system pressure to about 50 psi. The reaction is allowed to proceed for about 4 hours, or until the 125 g of ethylene oxide is reacted with the sucrose esters, and then the ethylene oxide feed is stopped. The initial reaction product is then cooled to 60° C. The initial reaction product now weighs approximately 225 g, which corresponds to an addition of, on average, 10 ethylene oxide groups on each of the four available hydroxyl groups.

The initial reaction product is then washed with 50 g of water at 60° C. The water and initial reaction product are gently stirred for approximately 10 minutes, and the resulting mixture is centrifuged. The top phase is decanted and retained and the bottom, aqueous phase is discarded.

The purified alkoxylated sucrose ester is analyzed and contains: greater than 99.9% Alkoxylated Sucrose Ester; less than 0.01% aldehyde; less than 0.01% ketones; less than 0.01% benzyl halide; less than 0.01% mono-benzyl ether; less than 0.01% acetals; and less than 0.01% ketals.

Example 3

Approximately 100 g of sucrose esters with an average degree of esterification of about 6 are prepared according to Rizzi and Taylor, U.S. Pat. No. 3,963,699. The sucrose esters are then placed in a reactor, and 1 g of sodium/potassium alloy is added to the reactor. The mixture is heated to 110° C. and 45 g of ethylene oxide is gradually fed into the reactor to maintain the system pressure to about 50 psi. The reaction is allowed to proceed for about 4 hours, or until the 45 g of ethylene oxide is reacted with the sucrose esters, and then the ethylene oxide feed is stopped. The initial reaction product is then cooled to 60° C. The initial reaction product now weighs approximately 145 g, which corresponds to an addition of, on average, 10 ethylene oxide groups on each of the two available hydroxyl groups.

The initial reaction product is then washed with 40 g of ethanol at 60° C. The ethanol and initial reaction product are gently stirred for approximately 10 minutes, and the resulting mixture is centrifuged. The top phase is decanted and retained and the bottom, alcohol phase is discarded.

The alkoxylated sucrose ester product is then analyzed and contains less than 1% aldehydes; less than 1% ketones; less than 1% benzyl halide; less than 1% mono-benzyl ether; less than 1% acetals; and less than 1% ketals.

Example 4

Approximately 50 g of sucrose esters with an average degree of esterification of about 4 and approximately 50 g of sucrose esters with an average degree of esterification of about 7 are prepared according to Rizzi and Taylor, U.S. Pat. No. 3,963,699. The sucrose esters are then combined and then placed in a reactor, and 1 g of sodium/potassium alloy is added to the reactor. The mixture is heated to 90° C. and 60 g of ethylene oxide is gradually fed into the reactor to maintain the system pressure to about 50 psi. The reaction is allowed to proceed for about 4 hours, or until the 60 g of ethylene oxide is reacted with the sucrose esters, and then the ethylene oxide feed is stopped. The initial reaction product is then cooled to 60° C. The initial reaction product now weighs approximately 160 g.

The initial reaction product is then washed with 30 g of water at 60° C. The water and initial reaction product are gently stirred for approximately 10 minutes, and the resulting mixture is centrifuged. The top phase is decanted and retained and the bottom, aqueous phase is discarded.

The alkoxylated sucrose ester product is then analyzed and contains less than 1% aldehydes; less than 1% ketones; less than 1% benzyl halide; less than 1% mono-benzyl ether; less than 1% acetals; and less than 1% ketals.

Example 5

Approximately 100 g of sucrose esters with an average degree of esterification of about 5 are prepared according to Rizzi and Taylor, U.S. Pat. No. 3,963,699. The sucrose esters are then placed in a reactor, and 1 g of sodium/potassium alloy is added to the reactor. The mixture is heated to 100° C. and 63 g propylene oxide is gradually fed into the reactor to maintain the system pressure to about 50 psi. The reaction is allowed to proceed for about 2 hours, or until the 83 g propylene oxide is reacted with the sucrose esters, and then the propylene oxide feed is stopped. The initial reaction product is then cooled to 60° C. The initial reaction product now weighs approximately 163 g, which corresponds to an addition of, on average, 8 propylene oxide groups on each of the three available hydroxyl groups.

The initial reaction product is then washed with 40 g of water at 60° C. The water and initial reaction product are gently stirred for approximately 10 minutes, and the resulting mixture is centrifuged. The top phase is decanted and retained and the bottom, aqueous phase is discarded.

The alkoxylated sucrose ester product is then analyzed and contains less than 1% aldehydes; less than 1% ketones; less than 1% benzyl halide; less than 1% mono-benzyl ether; less than 1% acetals; and less than 1% ketals.

Example 6

Approximately 100 g of sucrose esters with an average degree of esterification of about 2 are prepared according to Osipow et al, U.S. Pat. No. 4,380,616. The sucrose esters are dissolved in 300 g of dimethyl sulfoxide and the mixture is then placed in a reactor. To this is added 2 g of sodium/potassium alloy. The mixture is heated to 90° C. and 300 g ethylene oxide is gradually fed into the reactor to maintain the system pressure at about 50 psi. The reaction is allowed to proceed for 2 hours, or until the 300 g ethylene oxide is reacted with the sucrose esters, and then the ethylene oxide feed is stopped. The initial reaction product is then cooled to 60° C. The initial reaction product, including the solvent, now weighs approximately 700 g, which corresponds to an addition of, on average, 10 ethylene oxide groups on each of the six available hydroxyl groups.

The initial reaction product is then purified by sparging with nitrogen at 60° C. for 1 hour.

The alkoxylated sucrose ester product is then analyzed and contains less than 1% aldehydes; less than 1% ketones; less than 1% benzyl halide; less than 1% mono-benzyl ether; less than 1% acetals; and less than 1% ketals.

What is claimed is:

1. An alkoxylated sucrose ester composition with increased purity, wherein the alkoxylated sucrose ester composition comprises:
   a) at least one alkoxylated sucrose ester having the following structure:

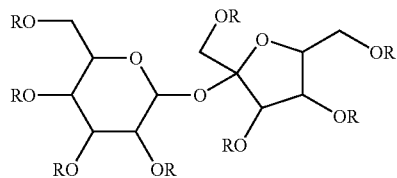

wherein R is independently selected from:
      i) COR';
      ii) $(CH_2CH_2O)_xH$; and
      iii) $(CH_2CH_2O)_x COR'$;
   wherein R' is a fatty acid compound having from 2 to 28 carbon atoms; and x is a number selected from 1 to 50;
   wherein at least one of the R groups is an ester group that is directly esterified to the sucrose backbone;
   wherein the alkoxylated sucrose ester is a hexa or hepta ester; and
   b) wherein the alkoxylated sucrose ester composition further comprises:
      i) less than 1% aldehydes;
      ii) less than 1% ketones;
      iii) less than 1% benzyl halide;
      iv) less than 1% mono-benzyl ether;
      v) less than 1% acetals; and
      vi) less than 1% ketals; and
   wherein the alkoxylated sucrose ester composition is substantially free of solvent.

2. A lubricating composition according to claim 1 wherein the composition further comprises water.

3. A lubricating composition according to claim 2 wherein the composition further comprises water.

4. A surfactant composition comprising an alkoxylated sucrose ester composition according to claim 1 and an additional surfactant selected from amine oxides, fatty alcohols, alkoxylated alcohols, sulfated alcohols, alkoxylated sulfated alcohols, and mixtures thereof.

5. An emulsifier composition comprising an alkoxylated sucrose ester composition according to claim 1 and an emulsifier selected from glycerine esters, sorbitan esters, and mixtures thereof.

6. A food composition comprising an alkoxylated sucrose ester composition according to claim 1 and an additional sucrose ester.

7. A laundry composition comprising an alkoxylated sucrose ester composition according to claim 1 and further comprising an additional material selected from amines, cationic amines, water, and mixtures thereof.

8. A purified alkoxylated sucrose ester composition, wherein the composition comprises:
   a) an alkoxylated sucrose ester having the following structure:

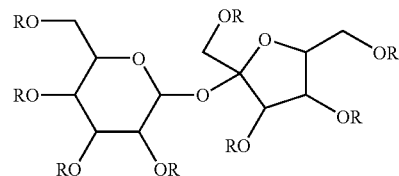

wherein R is independently selected from:
      i) COR';
      ii) $(CH_2CH_2O)_xH$; and
      iii) $((CH_2CH_2O)_x COR'$;
   wherein R' is a fatty acid compound having from 2 to 28 carbon atoms; and x is a number selected from 1 to 50;
   wherein at least one of the R groups is an ester group that is directly esterified to the sucrose backbone;
   wherein the alkoxylated sucrose ester is a hexa or hepta ester; and
   b) wherein the alkoxylated sucrose ester composition further comprises:
      i) less than about 100 ppm aldehydes;
      ii) less than about 100 ppm ketones;
      iii) less than about 100 ppm benzyl halide;
      iv) less than about 100 ppm mono-benzyl ether;
      v) less than about 100 ppm acetals;
      vi) less than about 100 ppm ketals; and
   wherein the alkoxylated sucrose ester composition is substantially free of solvent.

9. A lubricating composition comprising an alkoxylated sucrose ester composition or mixtures thereof according to claim 8 and an additional lubricant selected from olefins, paraffins, and mixtures thereof.

10. A lubricating composition according to claim 9 wherein the composition further comprises water.

11. A surfactant composition comprising an alkoxylated sucrose ester composition according to claim 8 and an additional surfactant selected from amine oxides, fatty alcohols, alkoxylated alcohols, sulfated alcohols, alkoxylated sulfated alcohols, and mixtures thereof.

12. An emulsifier composition comprising an alkoxylated sucrose ester composition according to claim 8 and an emulsifier selected from glycerine esters, sorbitan esters, and mixtures thereof.

13. A food composition comprising an alkoxylated sucrose ester composition according to claim 8 and an additional sucrose ester.

14. A laundry composition comprising an alkoxylated sucrose ester composition according to claim 8 and further comprising an additional material selected from amines, cationic amines, water, and mixtures thereof.

15. A purified alkoxylated sucrose ester composition, wherein the composition comprises:
   a) an alkoxylated sucrose ester having the following structure:

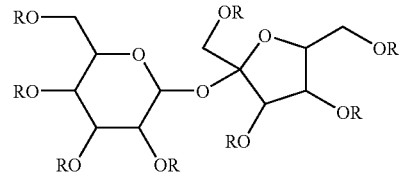

wherein R is independently selected from:
  ii) COR';
  iii) $(CH_2CH_2O)_xH$; and
  iv) $((CH_2CH_2O)_x COR')$;
wherein R' is a fatty acid compound having from 2 to 28 carbon atoms; and x is a number selected from 1 to 50;
wherein at least one of the R groups is an ester group that is directly esterified to the sucrose backbone;
wherein the alkoxylated sucrose ester is a hexa or hepta ester; and
b) wherein the alkoxylated sucrose ester composition is:
  i) free of aldehydes;
  ii) free of ketones;
  iii) free of benzyl halide;
  iv) free of mono-benzyl ether;
  v) free of acetals;
  vi) free of ketals; and
wherein the alkoxylated sucrose ester composition is substantially free of solvent.

16. A lubricating composition comprising an alkoxylated sucrose ester composition or mixtures thereof according to claim 15 and an additional lubricant selected from olefins, paraffins, and mixtures thereof.

17. A surfactant composition comprising an alkoxylated sucrose ester composition according to claim 15 and an additional surfactant selected from amine oxides, fatty alcohols, alkoxylated alcohols, sulfated alcohols, alkoxylated sulfated alcohols, and mixtures thereof.

18. An emulsifier composition comprising an alkoxylated sucrose ester composition according to claim 15 and an emulsifier selected from glycerine esters, sorbitan esters, and mixtures thereof.

19. A food composition comprising an alkoxylated sucrose ester composition according to claim 15 and an additional sucrose ester.

20. A laundry composition comprising an alkoxylated sucrose ester composition according to claim 15 and further comprising an additional material selected from amines, cationic amines, water, and mixtures thereof.

* * * * *